(12) United States Patent
Konawa

(10) Patent No.: US 7,982,091 B2
(45) Date of Patent: Jul. 19, 2011

(54) ABSORBENT ARTICLE

(75) Inventor: Satoko Konawa, Sakura (JP)

(73) Assignee: Daio Paper Corporation, Ehime (JP)

( * ) Notice: Subject to any disclaimer, the term of this patent is extended or adjusted under 35 U.S.C. 154(b) by 990 days.

(21) Appl. No.: 11/791,918

(22) PCT Filed: Nov. 29, 2005

(86) PCT No.: PCT/JP2005/021850
§ 371 (c)(1),
(2), (4) Date: Jul. 2, 2007

(87) PCT Pub. No.: WO2006/059588
PCT Pub. Date: Jun. 8, 2006

(65) Prior Publication Data
US 2008/0065037 A1 Mar. 13, 2008

(30) Foreign Application Priority Data
Nov. 30, 2004 (JP) ................................. 2004-346663

(51) Int. Cl.
*A61F 13/15* (2006.01)
*A61F 13/20* (2006.01)
(52) U.S. Cl. .......................... 604/380; 604/379; 428/156
(58) Field of Classification Search ............. 604/385.24–385.27, 380; 424/156
See application file for complete search history.

(56) References Cited

U.S. PATENT DOCUMENTS
4,059,114 A 11/1977 Richards
2003/0144644 A1* 7/2003 Murai et al. ............. 604/385.27

FOREIGN PATENT DOCUMENTS
| JP | 10-272155 | 10/1998 |
| JP | 10-328232 | 12/1998 |
| JP | 11-33054 | 2/1999 |
| JP | 2001-95842 | 4/2001 |
| JP | 2002-238948 | 8/2002 |
| JP | 2004-181084 | 7/2004 |

* cited by examiner

*Primary Examiner* — Melanie J Hand
(74) *Attorney, Agent, or Firm* — Jordan and Hamburg LLP

(57) ABSTRACT

An absorptive article includes a centrally high portion formed in the widthwise central portion of a napkin and made high on the side of a using face and a pair of left and right embosses formed individually on the two sides of the centrally high portion and extending substantially in the longitudinal direction of the napkin. The paired left and right embosses include a first bulging emboss having its individual emboss lines so formed of curves having centers of curvature on the center side of the napkin as to form an enlarged area of the emboss spacing width and a second bulging emboss having its individual emboss lines so formed of curves having centers of curvature on the center side of the napkin as to continue to the rear portion of the first bulging emboss through an intermediate arcuate emboss formed of curves having centers of curvature on the outer side of the napkin.

6 Claims, 8 Drawing Sheets

ABSORBENT ARTICLE

BACKGROUND OF THE INVENTION

The present invention relates to an absorptive article such as a sanitary napkin, a panties liner or an incontinence pad and, more particularly, to an absorptive article for improving the contact with the body of a user thereby to eliminate the back leakage.

In the absorptive article known in the prior art, such as the panties liner, the sanitary napkin or the incontinence pad, an absorber made of cotton-like pulp is sandwiched between a liquid-impermeable back sheet of a polyethylene sheet or a polyethylene sheet laminate nonwoven fabric and a liquid-permeable top sheet of a nonwoven fabric or a liquid-permeable plastic sheet.

Various improvements have been made on the absorptive article of this kind to make various means for preventing the leakage of a bodily fluid. One of these bodily fluid leakage preventing means is a technique in which grooves are formed of heat embosses together with a centrally high portion of the absorber. In Patent Document 1, for example, there is proposed a technique in which a homogeneously laminated absorber of pulp is pressed and deformed with a fit emboss contouring the centrally high portion to form the centrally high portion and in which a leakage preventing groove is formed around the centrally high portion thereby to prevent the diffusion (or leakage) of the bodily fluid.

In Patent Document 2, moreover, there is disclosed an absorptive article including a liquid-permeable layer on the side to abut against the skin of a user, a liquid-impermeable layer on the side not to abut against the skin, and an absorbing portion sandwiched between said liquid-permeable layer and said liquid-impermeable layer. The absorptive article includes a rising portion rising from the central portion of the absorbing portion to the side of the skin abutting face and extending in the longitudinal direction of said absorptive article and one or more rows of grooves formed on the side not to abut against the skin of said absorbing portion corresponding to said rising portion and extending in the longitudinal direction of said absorptive article.

In Patent Document 3, moreover, there is proposed a sanitary napkin including: an absorptive element for receiving a bodily fluid from the side of a using face and holding the same therein; a leakage preventing sheet disposed on the back side for preventing the leakage of the bodily fluid from said absorptive element to the back side; and gather cuffs having an elastically shrinking member for a gather cuff sheet disposed at the longitudinally intermediate portion of the product and on the two side portions of the product and raised on the skin side of the user by the shrinking force of the elastically shrinking member when the product is mounted. Said absorptive element has a centrally high portion extending in the longitudinal direction across a blood extrusion portion and made high at the widthwise central portion on the side a widthwise central portion. Said gather cuffs are constituted such that their shrinking forces may act over the longitudinal range corresponding to the range across at least the blood extrusion portion. Embosses are formed on the two sides of said centrally high portion of said absorptive element and over the length range across at least the blood extrusion portion. Those embosses are formed into such a shape at the blood extrusion portion as to bulge widthwise outward from the front and the back.

Patent Document 1: JP-A-11-33054
Patent Document 2: JP-A-10-328232
Patent Document 3: JP-A-2001-95842

All the inventions of the aforementioned Patent Documents 1 to 3 eliminate the leakage of menses or the like by fitting the absorber on the body shape of the blood extrusion portion. However, the rising shapes of the individual absorbers are formed of simple shapes composed of single arcuate curves.

As a matter of fact, however, the shape of the blood extrusion portion of a woman is complicated. Even if the absorber can be held in substantial contact with the vicinity of the blood extrusion port of the woman, the perineal region from the vaginal opening to the anus on the back side has a stereo shape of a pit so that the absorber cannot be held in contact with the perineal region. As a result, the menses or the like, which could not be absorbed in the vicinity of the blood extrusion port, may not be absorbed by the perineal region thereby to cause the back leakage.

Therefore, a main object of the invention is to provide an absorptive article for bringing an absorber into close contact with not only the blood extrusion port but also the vaginal opening of a woman thereby to improve the contact with the body.

In order to solve the aforementioned problems, according to a first aspect of the invention, there is provided an absorptive article having an absorber sandwiched between a liquid-permeable top sheet and a back sheet, characterized:

in that said absorber includes a centrally high portion in the widthwise central portion of said absorptive article and made high on the side of a using face, and a pair of left and right embosses formed individually on the two sides of said centrally high portion and extending substantially in the longitudinal direction of said absorptive article; and in that said paired left and right embosses include a first bulging emboss having its individual emboss lines so formed of curves having centers of curvature on the center side of the absorptive article as to form an enlarged area of the emboss spacing width, and a second bulging emboss having its individual emboss lines so formed of curves having centers of curvature on the center side of the absorptive article as to continue to the rear portion of said first bulging emboss through an intermediate arcuate emboss formed of curves having centers of curvature on the outer side of the absorptive article.

According to a second aspect of the invention, there is provided an absorptive article in accordance with the first aspect of the invention in which the absorber further includes a reduced shape emboss having its individual emboss lines so formed of curves having centers of curvature on the outer side of the absorptive article as to continue to the front side of said first bulging emboss and to form a reduced area of the emboss spacing width.

According to a third aspect of the invention, there is provided an absorptive article of the first or second aspect of the invention in which the absorber further includes a rear side emboss formed to continue to the rear side of said second bulging emboss and extending substantially along the longitudinal direction of the absorptive article and a third bulging emboss having its emboss lines so formed of curves having centers of curvature on the center side of the absorptive article as to form an enlarged area of the emboss spacing width at intermediate positions closer to the rear side of the rear side emboss.

According to a fourth aspect of the invention, there is provided an absorptive article of any of the first to third aspects of the invention in which the absorber further includes an auxiliary emboss so formed at the widthwise center portion of the absorptive article corresponding to said intermediate arcuate emboss as to extend substantially along the widthwise direction of the absorptive article.

According to a fifth aspect of the invention, there is provided an absorptive article according to the third or fourth aspect of the invention in which the absorber further includes second rear side embosses so individually formed on the outer sides of and at a spacing from said rear side emboss as to extend in the longitudinal direction of the absorptive article.

According to the invention thus far detailed, the second bulging emboss is formed to continue to the rear side of the first bulging emboss through the intermediate arcuate emboss. As a result, the absorber can be held in close contact with not only the blood extrusion port of a woman but also the perineal region. As a result, the contact with the body can be improved better than the product of the prior art so that the back leakage can be reliably prevented.

A mode of embodiment of the invention is described in detail in the following with reference to the accompanying drawings.

DETAILED DESCRIPTION OF THE INVENTION

Figure 1:
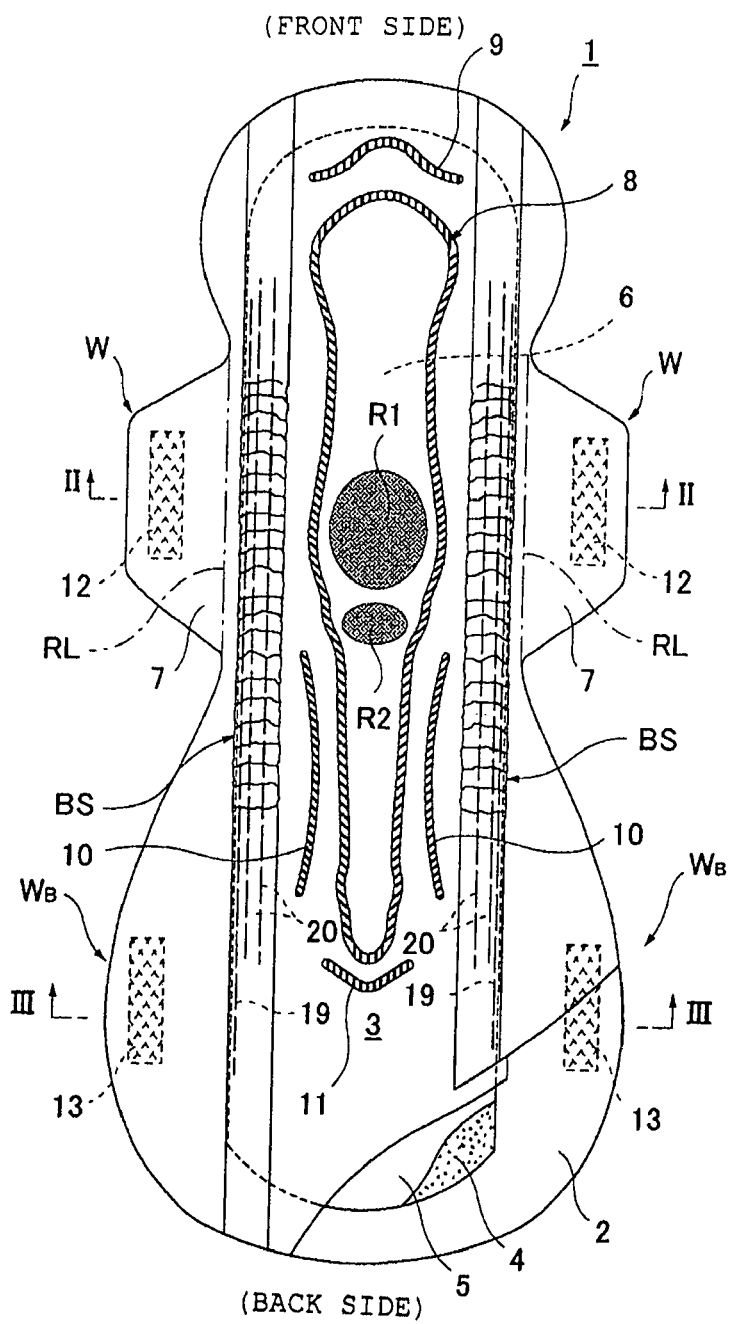
FIG. 1 is a development of a sanitary napkin 1 of the invention.
Figure 2:
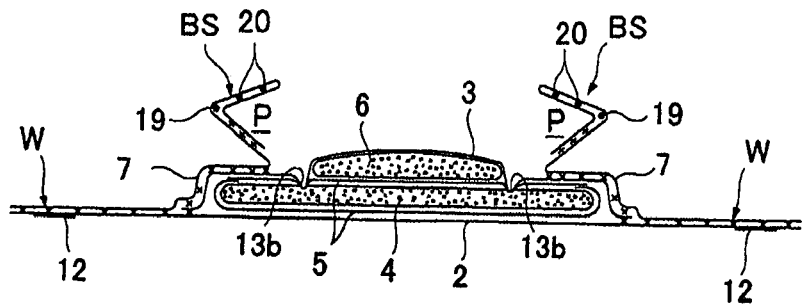
FIG. 2 is a transverse sectional view of the same (as taken along line II-II of FIG. 1).
Figure 3:
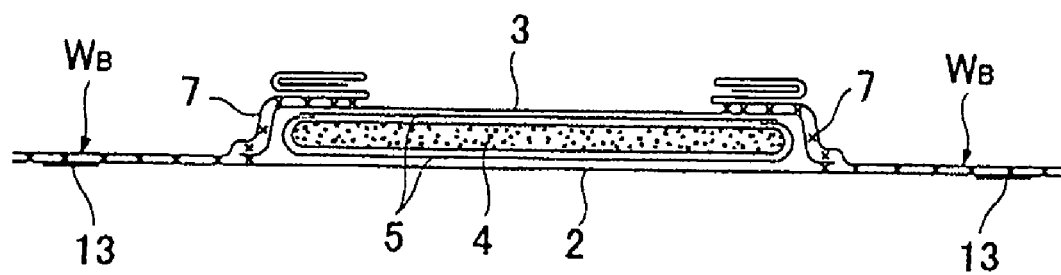
FIG. 3 is a transverse sectional view of the same (as taken along line III-III of FIG. 1).

FIG. 1 is a development of the sanitary napkin 1 according to a first mode of embodiment of the invention; FIG. 2 is a view along line II-II of FIG. 1; and FIG. 3 is a view along line III-III of FIG. 1.

The sanitary napkin 1 is constituted mainly of: a liquid-impermeable back sheet 2 made of a polyethylene sheet; a liquid-permeable top sheet 3 for quick permeation thereinto of menses or vaginal extrusions quickly; absorbents 4 and 6 sandwiched between those two sheets 2 and 3 and made of cotton-like pulp or synthetic pulp; a crepe paper 5 for enclosing the absorbent 4 so as to hold the shape of and improve the diffusivity of the absorbent 4; and a pair of left and right stereo gathers BS and BS rising from the substantial side edge portions of the absorber 4 and protruding within a predetermined longitudinal section from the surface side in a manner to cover at least a bodily fluid extruding portion. The absorber 4 is jointed, therearound at its upper and lower end edge portions, to the outer edge portions of the liquid-impermeable back sheet 2 and the liquid-permeable top sheet 3 by an adhesive such as a hot melt or adhering means such as a heat seal. The absorber 4 is jointed at its two side edge portions to the liquid-impermeable back sheet 2 extending sideways from the absorber 4 and side nonwoven fabrics 7 forming the stereo gathers BS by the adhesive such as the hot melt or the adhering means such as the heat seal. The laminate sheet portions of those liquid-impermeable back sheet 2 and the side nonwoven fabrics 7 form not only wing-shaped flaps W and W protruding sideways but also second wing-shaped flaps $W_B$ and $W_B$ at their portions located closer to the buttock side.

The structure of the sanitary napkin 1 is described in more detail in the following.

The liquid-impermeable back sheet 2 is made of a sheet material having at least liquid-impermeability such as polyethylene. In the tendency of recent years, however, a moisture-permeable sheet material is used from the viewpoint of preventing stuffiness. This water-repellent/moisture-permeable sheet is properly exemplified by a finely porous sheet which is produced by melting and blending an inorganic filler into an olefin-family resin such as polyethylene or polypropylene thereby to form a sheet and then by orienting the sheet uniaxially or biaxially. On the unused face side (or the outer face) of the liquid-impermeable back sheet 2, there are formed one or more rows of adhesive layer (although not shown) for fixing the sanitary napkin 1 on underwear when the sanitary napkin 1 is worn. The liquid-impermeable back sheet 2 may also be exemplified by a poly-laminate nonwoven fabric having a plastic film and a nonwoven fabric laminated.

The liquid-permeable top sheet 3 is preferably exemplified by a porous or non-porous nonwoven fabric or a porous plastic sheet. The material fibers composing the nonwoven fabric can be exemplified not only by synthetic fibers of an olefin family such as polyethylene or polypropylene, a polyester family, a polyester family or a polyamide family but also by regenerated fibers such as rayon or cupuro-ammonium rayon, or natural fibers such as cotton. The nonwoven fabric can be prepared by a suitable working method such as a spun lace method, a spun bond method, a thermal bond method, a melt-blown method or a needle punch method. Of these working methods, the nonwoven fabric by the spun lace method is excellent in softness and rich drape, and the nonwoven fabric by the thermal bond method is excellent in bulkiness and softness. Moreover, the liquid-permeable top sheet 3 can absorb, in case it is formed with numerous pores, the menses or vaginal extrusions (as will be called the "bodily fluid") quickly so that it can be excellent in the dry touch.

The absorber 4 may be any if it can absorb/hold the bodily fluid, and is usually exemplified for its absorbing function and price by the mixture which is prepared by mixing water-absorptive polymer powder into fluffed pulp. It is desired that the absorber 4 is enclosed by the crepe paper 5 so as to hold its shape or the like.

On the using face side of the absorber 4, the centrally high portion 6, which is high on the using face side and made of the absorber, is formed in the area which is defined by an emboss 8, which is formed at the widthwise central portion, made slender in the napkin longitudinal direction and closed in the peripheral direction. The centrally high portion 6 has a thickness of 3 to 20 mm, preferably 5 to 15 mm, because an excessive thickness raises the rigidity of the absorber 4 and deteriorates the close contact. On the using face side, moreover, embosses 9, 10 and 11 are individually formed together with the emboss 8. These embosses 8 to 11 are described in more detail hereinbelow.

On the other hand, the width size of the liquid-permeable top sheet 3 is made sufficiently longer than the width of the absorber 4 so as to cover only the absorber 4, as shown in the transverse sections of FIG. 2 and FIG. 3. The stereo gathers BS are made of the side nonwoven fabrics 7 different from the liquid-permeable top sheet 3, such as the nonwoven fabric, which has been subjected to a suitable water-repelling or hydrophilic treatment according to a purpose for prevent the penetration of the menses or vaginal extrusions or for enhancing the skin feel. These side nonwoven fabrics 7 can be prepared of a material such as the natural fibers, the synthetic fibers or the regenerated fibers by a suitable working method. Preferably, the nonwoven fabric providing the air permeability while reducing weight per unit area is used to eliminate the stiffness and prevent the stuffiness. Specifically, it is desired to use the nonwoven fabric prepared to have a basic weight of 18 to 23 g/m$^2$. Moreover, a water-proofed nonwoven fabric which is coated with a waterproof material such as a silicone family, a paraffin family or an alkyl chromic chloride family waterproof material is properly used for preventing the permeation of the bodily fluid reliably.

Figure 9:
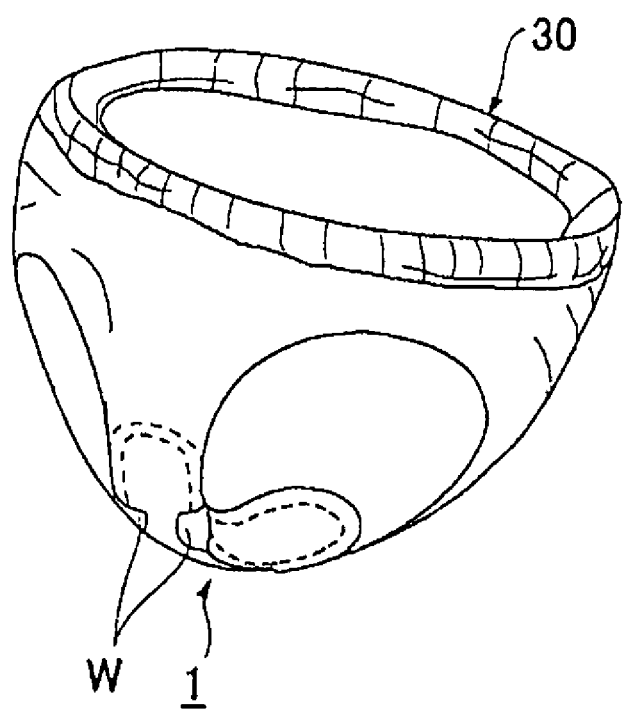
FIG. 9 is a perspective view showing the state, in which the napkin is mounted.

The side nonwoven fabrics 7 are adhered, as shown in FIG. 2 and FIG. 3, with the adhesive such as the hot melt at the outer side portions of the widthwise central portion over the range from the inner side positions of the absorber 4 exceeding the side edges to the outer edges of the liquid-impermeable back sheet 2. The resultant laminate sheet portions of those side nonwoven fabrics 7 and the liquid-impermeable back sheet 2 form the paired left and right wing-shaped flaps W and W at the positions of the absorber side portions substantially corresponding to the bodily fluid extrusion portions and form the second wing-shaped flaps $W_B$ and $W_B$ at the positions close to the buttock portion side. These wing-shaped flaps W and W and the second wing-shaped flaps $W_B$ and $W_B$ are provided on their individual outer face sides with adhesive layers 12, - - -, and so on, and 13, - - -, and so on. When the sanitary napkin is mounted in shorts 30, as shown in FIG. 9, the wing-shaped flaps W and W are folded back at the positions of cuffs RL, and are wrapped on the crotch portions of the shorts.

On the other hand, the inner side portions of the side nonwoven fabrics 7 are substantially doubly folded back. In these doubly folded sheets, there are arranged thread-like elastically stretchable members 19, which are fixed at their two ends or at suitable longitudinal positions in the intermediate portions in the height direction of the doubly folded sheets. A plurality of or two thread-like elastically stretchable members 20 and 20 are so arranged in the upper side portions of the thread-like elastically stretchable members 19 that their two ends or longitudinally suitable positions are fixed. These double sheet portions are adhered, at their front and back end portions, as shown in FIG. 3, in a folded laminate shape having a Z-shaped section, to the sides of the absorber 4. As a result, the stereo gathers BS and BS are formed to rise from the surface side while forming pockets P and P opened inward in the V-letter shape having the bending points at the portions arranging the thread-like elastically stretchable members 19.

[Emboss Structure]

Figure 4:
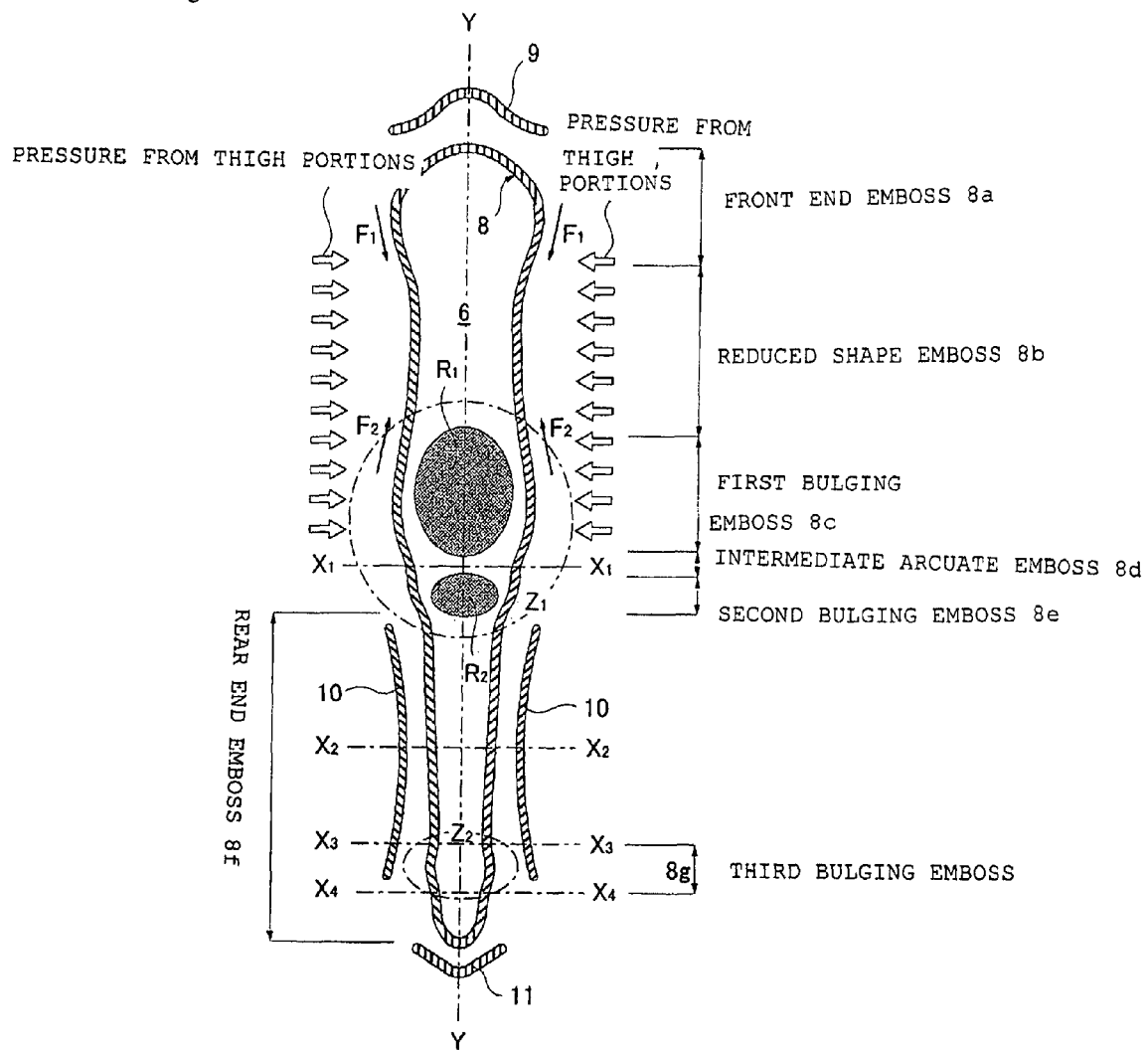
FIG. 4 is an explanatory view of embosses 8 to 11.

In the present sanitary napkin 1, as shown in detail in FIG. 4, the centrally high portion 6 of the absorber is formed at the widthwise central portion on the using face side, and the emboss 8 elongated in the longitudinal direction of the napkin 1 is formed around the centrally high portion 6. This emboss 8 is composed of a front end emboss 8a, a reduced shape emboss 8b, a first bulging emboss 8c, an intermediate arcuate emboss 8d, a second bulging emboss 8e and a rear end emboss 8f sequentially in the recited order from the front side. These individual embosses are formed not separately but continuously, and are closed as a whole in the peripheral direction. For purposes of directional reference when describing the portions of emboss 8, 'center side' refers to the area between left and right emboss lines (e.g., side with bumps R1, R2 and high portion 6). Similarly, the term 'outward side,' and 'outer sides' refers to portions of the article (e.g., napkin 1) to the outside of such left and right emboss lines (e.g., toward flaps W).

The front end emboss 8a is formed into such a generally semicircular shape that the paired left and right embosses formed on the two sides of the centrally high portion 6 and extending generally in the longitudinal direction merge into a curved line at the front end portion.

The reduced shape emboss 8b is composed of a pair of left and right emboss lines, which are continued from the front end emboss 8a and formed at the two sides of the centrally high portion 6 to extend in the longitudinal direction of the napkin 1. The reduced shape emboss 8b is positioned substantially on the front side of the thigh portions and is formed of such two side emboss lines as have centers of curvature on the outer side of the napkin 1 thereby to form an area having a reduced emboss spacing width, as shown.

The first bulging emboss 8c is composed of one pair of left and right emboss lines which are so formed continuously from the reduced shape emboss 8b and on the two sides of the centrally high portion 6 as to extend substantially in the longitudinal direction of the napkin 1. The first bulging emboss 8c is positioned substantially on the rear side of the thigh portions, and its two side emboss lines are so formed of curves having a center of curvature on the center side of the napkin 1 as to form an enlarged area of the emboss spacing width. The curves define respective bulges along the emboss lines as shown in FIG. 4.

Figure 5A:
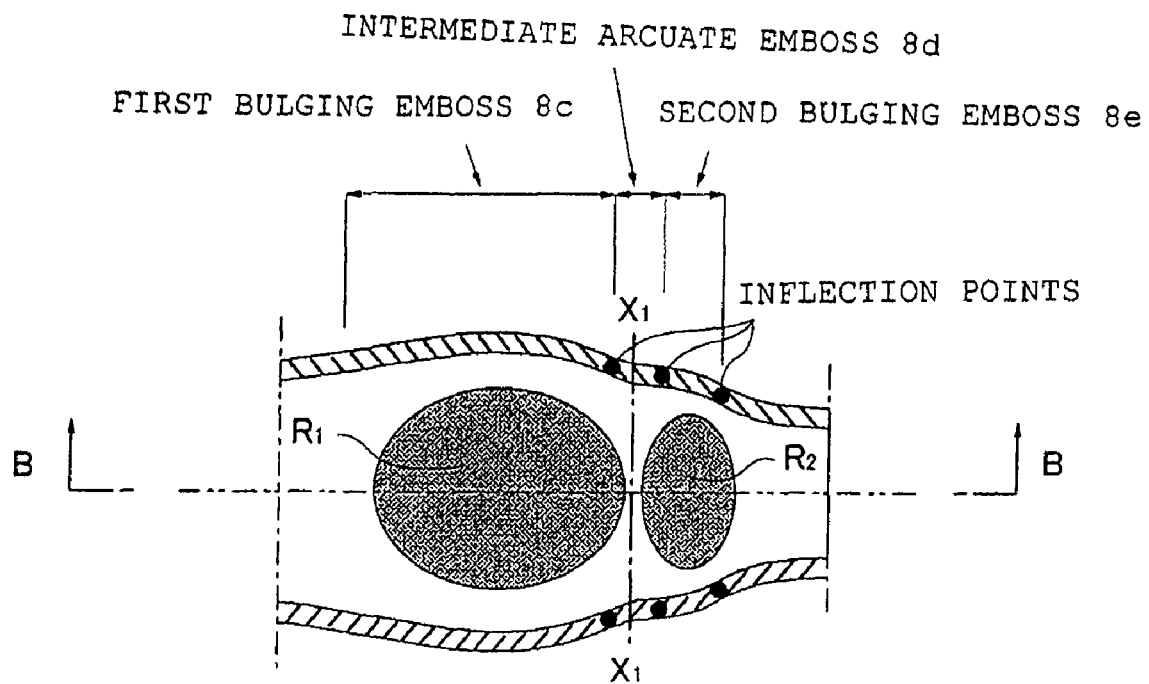
FIG. 5(A) is an enlarged view of an essential portion of the same.

The intermediate arcuate emboss 8d is composed of one pair of left and right emboss lines, which are so formed continuously from the first bulging emboss 8c and on the two sides of the centrally high portion 6 as to extend substantially in the longitudinal direction of the napkin 1. As shown in FIG. 5, more specifically, two side emboss lines are individually formed of curves having a center of curvature on the outer side of the napkin 1, within an extremely short section across the inflection points, at which the positions of the centers of curvature are inverted.

The second bulging emboss 8e is composed of one pair of left and right emboss lines which are so formed continuously from the intermediate arcuate emboss 8d and on the two sides of the centrally high portion 6 as to extend substantially in the longitudinal direction of the napkin 1. As shown in FIG. 5, more specifically, two side emboss lines are individually formed of curves having a center of curvature on the center side of the napkin 1, across the inflection points, at which the positions of the centers of curvature are inverted. The curves define respective bulges along the emboss lines, as shown in FIGS. 4 and 5. As compared with the first bulging emboss 8c, the second bulging emboss 8e is formed over a relatively short section width.

The rear end emboss 8f is composed of one pair of left and right emboss lines, which are so formed continuously from the second bulging emboss 8e and on the two sides of the centrally high portion 6 as to extend substantially in the longitudinal direction of the napkin 1. In the shown example, the emboss lines are so extended to the rear side that the emboss spacing width is gradually narrowed little by little and are jointed on the two sides by an arcuately curved emboss on the rear side. At the intermediate positions close to the rear side of the rear end emboss 8f, a third bulging emboss 8g is so formed of curves having centers of curvature on the central side of the napkin 1 that the emboss spacing width may be enlarged. The curves define respective bulges along the emboss lines, as shown in FIG. 4.

On the outer sides of the rear end of the rear end emboss 8f, there are formed the second rear side embosses 10 and 10, which are extended in the longitudinal direction of the napkin 1 while being spaced from the rear end emboss 8f. In the shown example, the two side embosses 10 are individually formed of arcuate curves having centers of curvature on the outer sides of the napkin 1.

Moreover, the front end independent emboss 9 of a general umbrella shape is formed at a spacing on the front side of the front end emboss 8a, and the rear end independent emboss 11 of a generally inverted umbrella shape is formed at a spacing on the rear side of the rear side emboss 8f.

The following effects can be attained according to the various embosses 8 to 11 thus formed.

At first, in the area forming the first bulging emboss 8c, the intermediate arcuate emboss 8d and the second bulging emboss 8e, as shown in detail in FIG. 5, the areas forming the individual bulging embosses 8c and 8e provide the areas which are hardly foldable by using the lines of the napkin widthwise direction as the flexible axes (or the folding lines) with the emboss lines bulging to the outer side. However, the intermediate arcuate emboss 8d, which is interposed between those bulging embosses 8c and 8e, has the emboss curves inverted so that they release the strain suppressing forces of the individual bulging embosses 8c and 8e. As a result, the bulging embosses 8c and 8e are easily folded relative to each other by using the line $X_1$-$X_1$ of the napkin widthwise direction as a flexible axis.

Figure 8:
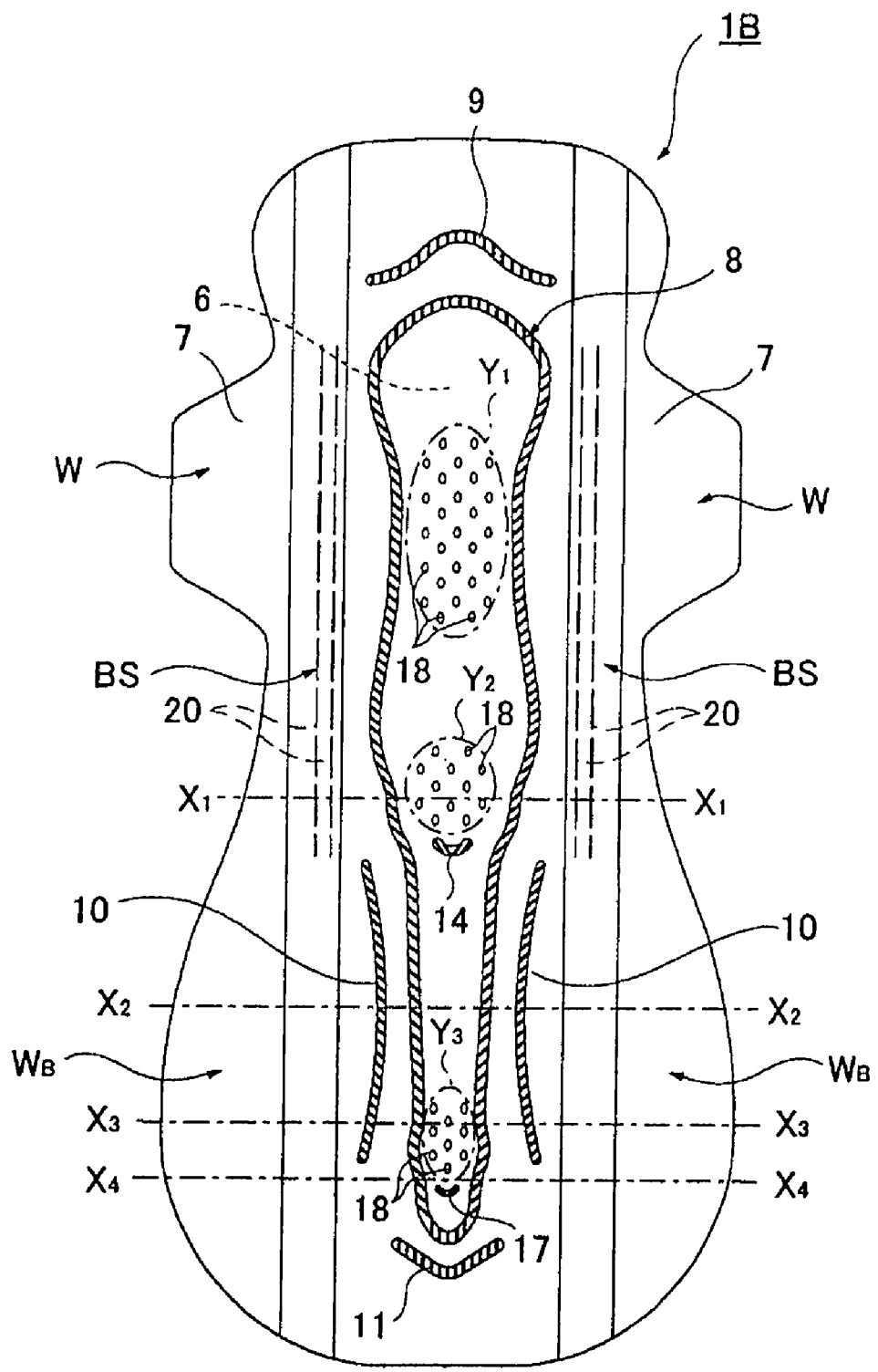
FIG. 8 is a development of a mode of forming another emboss.

When the napkin 1 is mounted in the shorts 30, as shown in FIG. 8, the area of the reduced shape emboss 8b and the first bulging emboss 8c receives a compressive force in the inward direction from the thigh portions. This compressive force compresses the absorber 4 in the widthwise direction. At the same time, the force is transmitted by the emboss 8 formed along the napkin longitudinal direction, so that inward action forces F1 and F2 act on the front side and the rear side, respectively. When the crotch portion of the shorts 30 is pulled up to the body, a pushing force to push the crotch portion is received along the longitudinal center line Y-Y by the napkin 1.

Under the action forces thus far described, in a $Z_1$ area, a first bump $R_1$ is formed at a portion, as corresponding to a blood extrusion port, of the first bulging emboss 8c. This bulge $R_1$ is brought into contact with the vicinity of the blood extrusion port so that it can absorb the menses or the like. At such a portion of the second bulging emboss 8e as corresponds to a perineal region from a vaginal opening to the vicinity of an anus on the rear side, a second bump $R_2$ is formed through the intermediate arcuate emboss 8d having the flexible axis $X_1$-$X_1$. This bump $R_2$ comes into close contact with the perineal region and absorbs the menses or the like, which could not be absorbed near the blood extrusion port reliably to prevent the bodily fluid reliably from leaking therealong to the rear side.

Figure 5B:
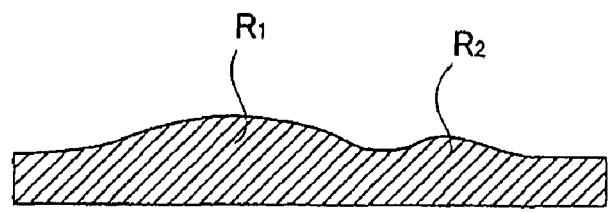
FIG. 5(B) is a view taken along line B-B.

As shown in FIG. 5(B), more specifically, the intermediate arcuate emboss 8d is released from the distortion in the rising direction. In the presence of the flexible axis $X_1$-$X_1$, moreover, the bumps $R_1$ and $R_2$ are so formed in the areas of the first bulging emboss 8c and the second bulging emboss 8e positioned in front of and at the back of the flexible axis that two mountains continue. The bump $R_1$ comes into close contact with the blood extrusion port and the bump $R_2$ comes into close contact with the perineal region so that they can prevent the menses or the like reliably from leaking therealong. Here, the bump $R_2$ is made so smaller than the bump $R_1$ as is proportional to the forming scale of the bulging emboss 8e.

In the rear end emboss 8f, on the other hand, the second rear side embosses 10 are formed in addition to the rear side embosses 8f individually on the two sides of the centrally high portion 6 along the longitudinal direction of the napkin 1. These four embosses in total form the flexible axes individually, so that the flexibility in the direction of an axis $X_2$-$X_2$ is improved to enhance the fit on the valley portion of the hips.

Moreover, the third bulging emboss 8g, which is formed at the position close to the rear side of the rear side emboss 8f, is made foldable at individual positions of transverse lines $X_3$-$X_3$ and $X_4$-$X_4$ corresponding to the positions of inflection, and the distortions in the longitudinal line Y-Y of the napkin are separated at the individual positions of the inflection points. As a result, an area $Z_2$ is raised to fit the valley portion of the hips.

On the other hand, the front end independent emboss 9 of the general umbrella shape, which is formed at the foremost end of the napkin 1, acts as the flexible axis to make the front end portion of the napkin 1 easily foldable. On the other hand, the rear end independent emboss 11 of the generally inverted umbrella shape, which is formed on the rear side, acts as the flexible axis to make the second left and right wind-shaped flaps $W_B$ and $W_B$ easily foldable.

Figure 6:
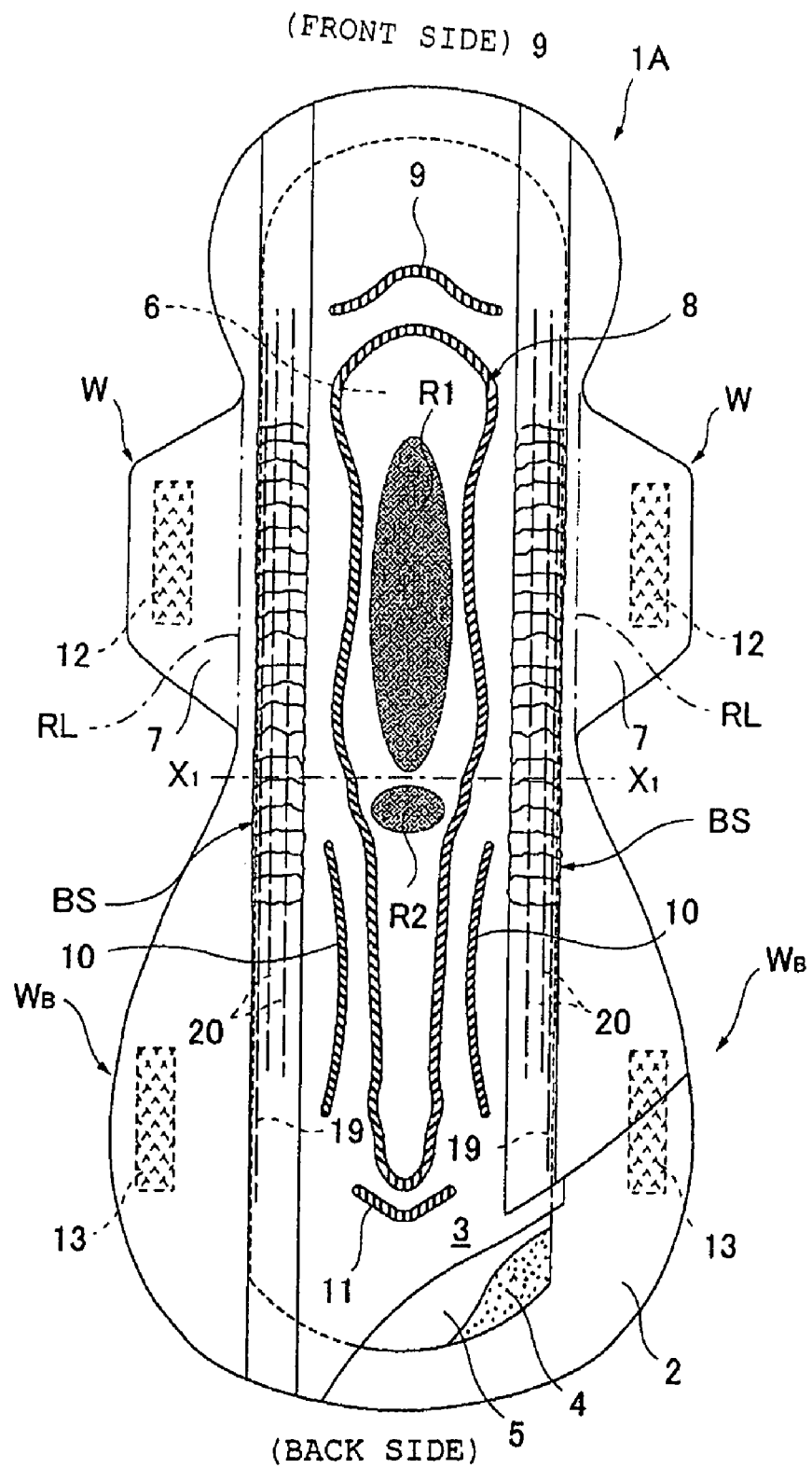
FIG. 6 is a development view of the sanitary napkin 1, in which the positions of the embosses 8 to 11 are moved to the lower side.

Here in the napkin 1, the position of the blood extrusion port is generally fixed at the portions corresponding to the positions of the wing-shaped flaps W and W. As shown in FIG. 6, for example, the various embosses 8 to 11 may be so relatively displaced to the lower side that the area of the reduced emboss 8b may be positioned to the positions corresponding to the wing-shaped flaps W and W.

Figure 7A:
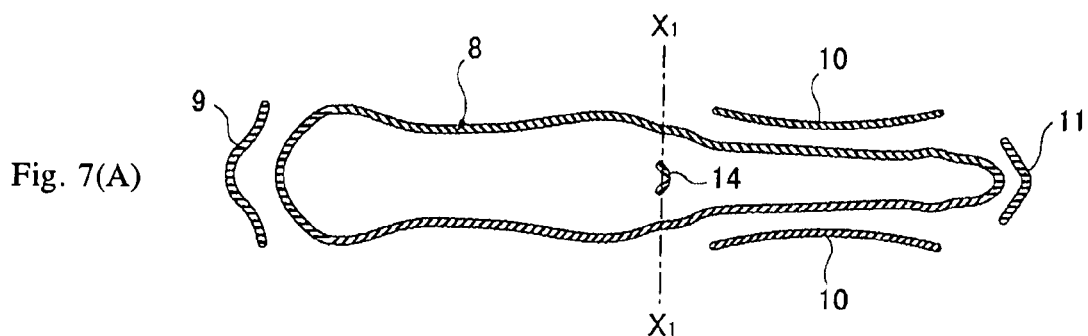
FIGS. 7(A) to 7(C) are views showing modifications of the emboss 8.
Figure 7B:
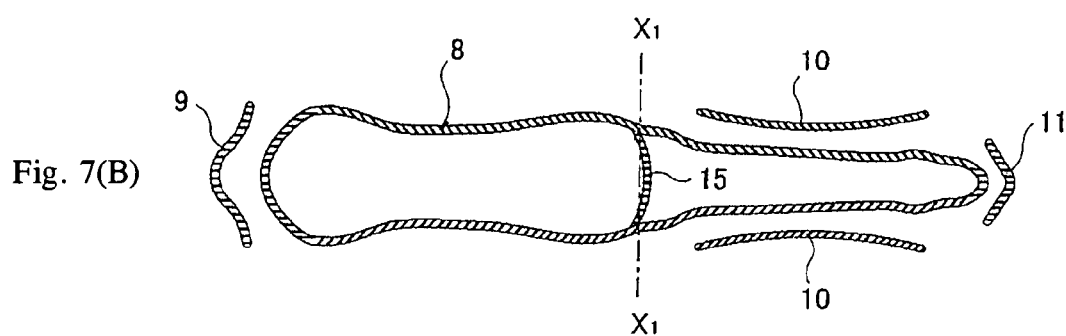

Other Modes of Embodiment (1) An auxiliary emboss along the generally widthwise direction of the napkin 1 may be added to make the napkin 1 easily foldable at the positions of the flexible axis $X_1$-$X_1$ which is formed between the area of the first bulging emboss 8c and the area of the second bulging emboss 8e. FIG. 7(A) shows an example in which an arcuate emboss 14 oriented in the widthwise direction is formed as the auxiliary emboss at the widthwise central portion. FIG. 7(B) shows an example in which an arcuate emboss 15 is formed in the widthwise direction to connect the embosses on the two sides.

Figure 7C:
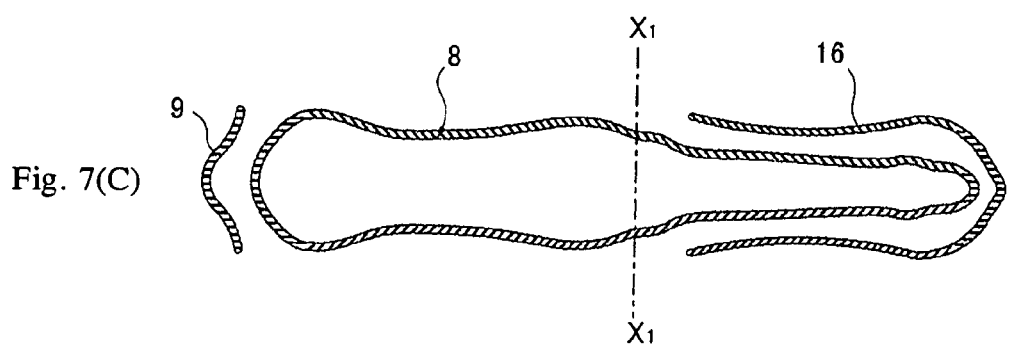

(2) In the aforementioned mode of embodiment, the second rear side embosses 10 and 10 are formed independently of each other. As shown in FIG. 7(C), however, the second rear side embosses 10 and 10 and the rear end independent emboss 11 may also be continued to form a generally U-shaped continuous emboss 16.

(3) As shown in FIG. 8, moreover, it is desired that the absorptivity of the menses is improved by forming a number of small recessed dot embosses 18, 18, - - -, and so on on the surface of the centrally high portion 6 of an area $Y_1$ including a blood extrusion portion, an area $Y_2$ including a perineal region corresponding portion, and an area $Y_3$ including the third bulging emboss 8g. In the example shown in FIG. 8, arcuate embosses 14 and 17 are so oriented in the widthwise direction at the widthwise central portion as to correspond to the adjoining position of the flexible axis $X_1$-$X_1$ and the portion the third bulging emboss 8g.

(4) In the aforementioned mode of embodiment, the emboss 8 is formed into the closed shape as a whole by jointing the paired left and right emboss lines at the front end portion and the rear end portion of the napkin. However, the paired left and right emboss lines may be formed in the mode where they are not jointed at the front end portion and/or at the rear end portion.

The invention claimed is:

1. An absorptive article comprising an absorber sandwiched between a liquid-permeable top sheet and a back sheet, wherein said absorber includes a pair of left and right embosses formed individually and extending substantially in the longitudinal direction of said absorptive article, the absorber having an area between the pair of left and right embosses including a first area of a first thickness and at least one second area of a second thickness thicker than said first thickness, said at least one second area located in a widthwise central portion of the absorbent article;

wherein said pair of left and right embosses define a first bulging emboss portion, the left emboss having a first bulge with a center of curvature to the article's center side of the left emboss, the right emboss having a first bulge with a center of curvature to the article's center side of the right emboss, the first bulging emboss portion defining an area of enlarged emboss spacing width;

wherein said pair of left and right embosses further define a second bulging emboss portion, the left emboss having a second bulge with a center of curvature to the article's center side of the left emboss, the right emboss having a second bulge with a center of curvature to the article's center side of the right emboss, the second bulging emboss portion defining an area of enlarged emboss pair spacing width, the second bulging emboss portion defined to continue to rearward of said first bulging emboss portion through an intermediate arcuate emboss, the intermediate arcuate emboss including a left side portion having a center of curvature to the article's outward side of the left emboss and a right side portion having a center of curvature to the article's outward side of the right emboss; and wherein said pair of left and right embosses further define a reduced shape emboss longitudinally frontal to the first bulging emboss portion in an area with reduced spacing width between the left and right embosses, the reduced shape emboss portion including a left side portion formed by a portion of the left emboss and having a center of curvature to the article's outward side of the left emboss and a right side portion formed by a portion of the right emboss and having a center of curvature to the article's outward side of the right emboss.

2. An absorptive article as set forth in claim 1, wherein said pair of left and right embosses further define:
 a rear side emboss portion, formed as a continuation to the rear side from said second bulging emboss portion and extending substantially along the longitudinal direction of the absorptive article, and
 a third bulging emboss portion formed toward a rear side along the rear side emboss portion, the left emboss having a third bulge with a center of curvature to the article's center side of the left emboss, the right emboss having a third bulge with a center of curvature to the article's center side of the right emboss, the third bulging emboss portion defining an area of enlarged emboss pair spacing width.

3. An absorptive article as set forth in claim 1 wherein the absorber further includes an auxiliary emboss extending in a widthwise direction and located central to said pair of left and right embosses in an area adjacent to said intermediate arcuate emboss.

4. An absorptive article as set forth in claim 2, wherein the absorber further includes second left and right rear side embosses extending in the longitudinal direction of the absorptive article and formed on the outer sides of and at a spacing from said paired right and left embosses in a vicinity of said rear side emboss.

5. An absorptive article as set forth in claim 3, wherein the absorber further includes second left and right rear side embosses extending in the longitudinal direction of the absorptive article and formed on the outer sides of and at a spacing from said paired right and left embosses.

6. An absorptive article as set forth in claim 1, wherein a first one of said at least one second area is located in the widthwise central portion of the absorbent article adjacent to the first bulging emboss portion.

* * * * *